United States Patent [19]

Klose

[11] 4,118,443

[45] Oct. 3, 1978

[54] PRODUCTION OF ACID PHOSPHORIC ACID ESTER SALTS

[75] Inventor: Werner Klose, Erfstadt, Fed. Rep. of Germany

[73] Assignee: Hoechst Aktiengesellschaft, Frankfurt am Main, Fed. Rep. of Germany

[21] Appl. No.: 761,054

[22] Filed: Jan. 21, 1977

[30] Foreign Application Priority Data

Jan. 22, 1976 [DE] Fed. Rep. of Germany ....... 2602289

[51] Int. Cl.² ................................................ C07F 9/09
[52] U.S. Cl. ............................ 260/980; 260/346.11; 260/429.9; 260/438.1; 260/439 R
[58] Field of Search .............. 260/980, 987, 429.9, 260/439 R, 438.1

[56] References Cited

U.S. PATENT DOCUMENTS

| | | | |
|---|---|---|---|
| 2,790,766 | 4/1957 | Otto | 260/980 X |
| 3,117,152 | 1/1964 | Michaels | 260/980 X |
| 3,584,087 | 6/1971 | Mausner et al. | 260/987 X |

*Primary Examiner*—Anton H. Sutto
*Attorney, Agent, or Firm*—Connolly and Hutz

[57] ABSTRACT

A product consisting essentially of an acid orthophosphoric acid ester salt and containing at most about 1 weight % of water is made. The ester group R contains 1 to 50 carbon atoms, and the salt-forming cation M is a mono- or bivalent metal ion or an ammonium ion. To make the product, molar proportions of $P_2O_5$ and of a compound of the general formulae $M_2O$, $M_2CO_3$, MO or $MCO_3$ are reacted at about 0° to 150° C, with thorough agitation, with $2/m$ mol of an at least partially liquid or molten organic hydroxyl compound of the general formula $R(OH)_m$, in which formulae the substituents M and R have the meanings given above and m is a number of 1 to 4. The reaction is terminated and the reaction product is cooled.

5 Claims, No Drawings

PRODUCTION OF ACID PHOSPHORIC ACID ESTER SALTS

Salts of acid phosphoric acid esters with mono- or bivalent cations find increasing use in the most various fields. Thus, for example, it has been suggested that long chain alkyl phosphates (cf. German Patent Specification DT-AS No. 1 263 213 and U.K. Specification No. 728 582) and phosphoric acid ester salts of alkylpolyglycol ethers and alkylarylpolyglycol ethers (cf. German Patent Specification DT-OS No. 2 008 777) be used in detergent compositions, particularly as foam regulators and corrosion inhibitors. The sodium salts (cf. German Patent Specification DT-OS No. 2 022 887) and the nickel salts of acid alkyl phosphates (cf. U.S. Pat. No. 3,313,658) have also been suggested for use as stabilizers for plastic materials. A further use the sodium salts of acid phosphoric acid esters of alkylpolyglycol ethers are put to is as wetting agents in herbicidal compositions (cf. U.S. Pat. No. 3,397,051), and the potassium salts of acid phosphoric acid esters find interesting use as preparation aids in the manufacture of synthetic fibers. It has finally been suggested that the sodium, magnesium and calcium salts of acid phosphoric acid esters be used as dissolving intermediaries in chemical cleaning compositions and that the nickel salts of these esters be used as fuel additives (cf. U.S. Pat. Nos. 3,334,978 and 3,445,206).

In many cases, where the phosphoric acid esters are put to practical use, it is necessary or at least desirable for them to be available in the form of anhydrous material. More particularly, in those cases, for example, in which the ester salts are admixed with further dry and pulverulent components to produce a composition, or in which they are dissolved in an anhydrous liquid being immiscible or partially miscible with water, it is highly desirable for the ester salts to combine flowability with pourability and storability.

The processes used heretofore for making salts of acid phosphoric acid esters with mono- or bivalent cations, wherein an acid phosphoric acid ester is neutralized, for example, by means of a suitable metal oxide, hydroxide or carbonate, are not fully satisfactory inasmuch as the final product is always obtained in admixture with water of neutralization set free during the reaction (cf. reaction equations 1 to 3 below) and, in those cases, in which the neutralizing agent is used in the form of an aqueous solution, also in admixture with solvent water. In the following equations 1 to 3, Me stands for a mono- or bivalent metal and R stands for an alkyl group, for example.

$$(RO)_2POOH + Me^I OH \rightarrow (RO)_2POOMe^I + H_2O \quad (1)$$

$$ROPO(OH)_2 + Me^I_2CO_3 \rightarrow ROPO(OMe^I)_2 + H_2O + CO_2 \quad (2)$$

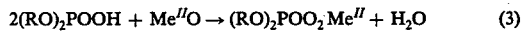

$$2(RO)_2POOH + Me^{II}O \rightarrow (RO)_2POO_2Me^{II} + H_2O \quad (3)$$

The processes described heretofore yield hydrous salts of phosphoric acid esters which generally have a pasty, glutinous, semisolid, wax-like or salvy consistency, and which must be freed, after preparation, from adhering water by additional expensive treatment. As described in German Patent Specification DT-OS No. 2 022 887, the products are dehydrated in a drum drier.

A still further process for making free-flowing ester salts has been described in German Patent Specification DT-OS No. 2 337 262, wherein the ester salt is admixed with considerable proportions of an inert filler, e.g. amorphous silicic acid, which is disadvantageous in respect of the following points: The content of active substance in the final flowable product is quite materially reduced and filler ballast which is inactive and even undesirable for the intended use goes into the product.

The present process, wherein it is unnecessary for the ester salt to be dried under unattractive conditions or to be admixed with special drying agents, is intended to avoid the disadvantageous effects described hereinabove.

The present invention now provides a process for making a product, which consists essentially of an acid orthophosphoric acid ester salt and contains at most about 1 weight % of water, and of which the inert ester group R (inert with respect to the reactants) being an optionally substituted alkyl, cycloalkyl, polyalkoxyalkyl, aryl, polyalkoxyaryl, alkaryl, or aralkyl group contains 1 to 50 carbon atoms, whereby the carbon chain or ring of the ester group R may contain oxygen, nitrogen, sulfur or phosphorus as a hetero-atom and the salt-forming cation M is a mono- or bivalent metal ion or an ammonium ion, which process comprises: reacting, at temperatures of about 0° to 150° C. with thorough agitation, molar proportions of $P_2O_5$ and of a compound of the general formulae $M_2O$, $M_2CO_3$, MO or $MCO_3$ with $2/m$ mol of an at least partially liquid or molten organic hydroxyl compound of the general formula $R(OH)_m$, terminating the reaction, cooling the resulting reaction product and pulverizing it, if desired, the substituents M and R having the meanings defined above and $m$ being a number of 1 to 4.

A preferred embodiment of the present process comprises using a compound of the general formulae $M_2O$, $M_2CO_3$, MO or $MCO_3$, in which M stands for an alkali metal or alkaline earth metal ion, for an alkyl or aryl-substituted ammonium ion, or for a bivalent cation selected from elements having an atomic number of 25 to 30. A further preferred embodiment provides for $P_2O_5$ to be reacted with an organic hydroxyl compound which is selected from stearyl alcohol, dodecyl alcohol, cyclohexanol, phenol, polyethylene glycol, isotridecyl alcohol, nonylphenolpolyglycol ether, an addition product of stearyl alcohol with 8 mols of ethylene oxide, a commercial mixture of partially branched aliphatic $C_{16}$–$C_{19}$ alcohols, or trishydroxymethylphosphine oxide.

The reactants are generally reacted at temperatures of 20° to 100° C., depending on the consistency of the particular organic hydroxyl compound used. The product made by the present process contains up to 1 weight % of water and at least about 85 weight % of acid orthophosphoric acid ester salt.

The following statements are intended further to illustrate the process of the present invention.

The acid phosphoric acid ester salts of the present invention can be made continuously or discontinuously in various installations which are selected in accordance with the consistency of the starting mixture, the mixture in the various reaction stages or the final product. In those cases in which the substances have a solid or pasty consistency, it is possible to react the starting materials discontinuously in a kneader, for example, which may be series-connected to a comminuting and screening device. For continuous reaction, it is preferable to use a single screw or double screw mixer provided with a heating and cooling device. Starting materials which are substantially in liquid form may also be reacted in a mixer provided with an agitator which is selected in accordance with the consistency of the mass to undergo reaction.

Critical factors with regard to continuous or discontinuous operation are inter alia the reactivity and consistency of the starting materials used. For example, if a hydroxyl compound, which is solid at room temperature, is used, e.g. stearyl alcohol, it is possible to mix the reactants together at a temperature below the fusion point of the hydroxyl compound and to react the resulting mixture by heating it with extreme caution. Failing this, resulting $CO_2$ may be found to partially convert the reaction melt to foam, to force the foam away from the reaction zone into other structural components of the installation used, and to with draw such foam from the reaction.

While it is possible to control the reaction by moderate supply of heat or by adding metered quantities of one of the reactants to the mixture of the two other reactants, the fact remains that this results in longer reaction periods and in the formation of salts of unesterified phosphoric acid in the reaction product.

To avoid these adverse effects, it is good practice to introduce the reactants continuously into a moderately heated reaction zone and, after termination of the reaction, to remove and cool the reaction product rapidly. In this case, the reaction mixture is delivered via a storage hopper to an extruder whose screw is surrounded by a heating jacket subdivided into a plurality of heating zones. By appropriately balancing the conveying capacity and zone temperatures against one another, it is possible for the product to be heated so that it is at reaction temperature just upstream of the extruder outlet. $CO_2$ which is set free causes the volume of the reaction mixture to be increased whereby it becomes possible for the product to pass rapidly through the hot reaction zone. Foam coming from the extruder die is delivered on to an appropriate cooling means, e.g. a cooling roller, belt or plate, where it solidifies to give a porous solid material which is easy to comminute to a product of low apparent density.

Depending on the particular nature of the various reactants forming the reaction mixture, they may be brought together in different manner. If hydroxyl compounds which are solid at room temperature are used, it is possible to mix the starting materials at room temperature and to react the resulting mixture by heating it.

It is also possible to jointly add phosphorus pentoxide and neutralizing agent to the hydroxyl compound preheated to reaction temperature. Another possiblity comprises introducing the hydroxyl compound into a mixture of phosphorus pentoxide and metal or ammonium compound. Finally, it is possible to admix phosphorus pentoxide with a mixture of hydroxyl compound and metal or ammonium compound.

As already mentioned above, the reaction temperature is selected in accordance with the consistency and reactivity of the organic hydroxyl compound used. The reaction temperature used for making the phosphoric acid ester salts of the present invention depends on the consistency and reactivity of the hydroxyl compound employed and generally is within the range 0° to 150° C., preferably 20° to 100° C.

In those cases in which liquid and very reactive hydroxyl compounds are used, it may be advantageous for the reaction mixture to be initially kept at temperatures of 20° to about 40° C. and, after the main reaction is complete, to be heated to 80° to 120° C. for completion of the whole reaction. Solid hydroxyl compounds generally undergo reaction only at temperatures close to their fusion points so that it is necessary for the reaction mixture to be heated to the necessary temperature and to be maintained at that temperature during the entire reaction period.

Typical representatives of organic hydroxyl compounds which are useful in the present process are the following:

(a) Aliphatic alcohols with 1 to 22 carbon atoms, e.g. methanol, ethanol, isopropanol, n-butanol, isobutanol, cyclohexanol, 2-ethylhexanol, n-dodecanol, isotridecyl alcohol, stearyl alcohol, oleyl alcohol and commercial mixtures thereof;

(b) aromatic hydroxyl compounds with 6 to 18 carbon atoms, e.g. phenol, cresols, xylenols, nonylphenols, benzyl alcohol and 2-phenylpropanol-1;

(c) addition products of an alkylene oxide with a hydroxyl compound, e.g. methyl glycol, ethyl glycol, butyl glycol, butyl diglycol, and more particularly addition products of: lauryl alcohol with 4 mols of ethylene oxide; stearyl alcohol with 8 mols of ethylene oxide; oleyl alcohol with 5 mols of ethylene oxide; phenol with 6 mols of ethylene oxide; and nonylphenol with 8 mols of ethylene oxide;

(d) polyhydric hydroxyl compounds, e.g. ethylene glycol, diethylene glycol, polyethylene glycol, glycerol, neopentyl glycol, trimethylol propane, hydroquionone, bisphenol A, and (e) hydroxyl compounds carrying substituents or heteroatoms in the C-skeleton, e.g. 3-methoxybutanol-1, furfuryl alcohol, thiodiglycol or tris-hydroxymethylphosphine oxide.

The products obtainable by the process of the present invention find very widespread uses, e.g. as foam regulators in detergent and cleaning compositions, as additives in metal processing liquids or preparation aids for synthetic fibers.

The products of the present invention are substantially anhydrous and therefore readily flowable and storable. Moisture which may adhere to the products, if any, corresponds to at most 1 weight % of water. The process of the present invention compares very favorably technically and commercially with the prior art methods inasmuch as it enables the products which incidentally need not be subjected to any additional drying operation to be made in a single step operation.

EXAMPLE 1

1080 g (4 mols) of stearyl alcohol, 212 g (2 mols) of anhydrous sodium carbonate and 284 g (2 mols) of phosphorus pentoxide were mixed together with the exclusion of moisture and at room temperature in a kneader and the resulting mixture was heated. At about 60° C., the mixture commenced softening and foaming while $CO_2$ was set free. By heating to 80° C., the reaction was continued until $CO_2$ ceased to be formed. A pasty product was obtained. It solidified on cooling to about 70° C. and it was finely pulverized by means of kneading tools. The ester salt contained 18.8 weight % of $P_2O_5$ (calculated: 19.1 weight %), 0.1 weight % of $CO_2$ and 0.7 weight % of water. The content of orthophosphate and pyrophosphate was determined by quantitative paper chromatographic analysis and found to be 6.9 weight %, calculated as $NaH_2PO_4$, and 5.6 weight %, calculated as $Na_2H_2P_2O_7$. The vibration density of a sieve fraction consisting of particles with a size of less than 1 mm was 718 g/liter.

EXAMPLE 2

11.61 kg (43 mols) of stearyl alcohol, 2.28 kg (21.5 mols) of anhydrous sodium carbonate and 3.05 kg (21.5 mols) of phosphorus pentoxide were mixed with the exclusion of moisture in a tumbling mixer and the resulting mixture was conveyed to the storage hopper of a BATTENFELD extruder. The extruder screw was jacketed to provide for two zones separately heatable electrically. The temperatures prevailing in the two zones and the number of revolutions of the screw were so balanced against one another that fully reacted product, which ceased to foam, left the extruder die at a temperature low enough for the issuing foam to solidify rapidly. To this end, a temperature of 50° to 60° C. was maintained in a first heating zone which was 20 cm long, a temperature of 75° to 80° C. was maintained in a second heating zone which was 20 cm long, and the screw was operated at a speed of 42–46 rpm.

The screw diameter was 20 mm. Under these conditions, 3–4 kg/h of reaction product was put through. The porous product was easy to pulverize. A sieve fraction consisting of particles with a size of less than 1 mm had a vibration density of 514 g/liter. The ester salt contained 18.3 weight % of $P_2O_5$, 1.3 weight % of $CO_2$ and 0.8 weight % of water.

EXAMPLE 3:

1 710 g of an addition product of stearyl alcohol and 8 mols of ethylene oxide, 254 g of $Na_2CO_3$ and 341 g of $P_2O_5$ were mixed in a kneader. The mixture underwent spontaneous heating to about 30° C. and a pasty product was obtained. The reaction was initiated by heating the mixture to 50° C. and completed by heating to 80° C. The product which solidified on cooling was crushed and ground by means of the kneader tools.

Sieve analysis of the ground product indicated the following particle sizes:
  89 weight % less than 1.5 mm,
  3 weight % 1.5 to 2 mm, and
  8 weight % more than 2 mm.

The product contained 0.9 weight % of water and 15.3 weight % of $P_2O_5$.

EXAMPLE 4

1808 g of lauryl alcohol and 515 g of anhydrous $Na_2CO_3$ were placed in a kneader, mixed and 691 g of $P_2O_5$ was added within 80 minutes by means of a dosing screw feeder. The temperature of the mixture was found to increase to 49° C. The mixture was heated to 70° C. and the resulting product was cooled and pulverized. The reaction product contained 24.5 weight % (calculated: 24.8 weight %) of $P_2O_5$ and 1 weight % of water. 1.2 weight % of the product was orthophosphate (calculated as $NaH_2PO_4$) and 5.5% was pyrophosphate (calculated as $Na_2H_2P_2O_7$).

EXAMPLE 5

The procedure was as described in Example 4, but 1507 g of lauryl alcohol was reacted with 560 g of $K_2CO_3$ and 575 g of $P_2O_5$. The ester salt obtained contained 23.0 weight % of $P_2O_5$ (calculated: 23.3 weight %) and 0.4 weight % of $CO_2$.

EXAMPLE 6

66 g of magnesium oxide was placed in a stirring flask and suspended in 2000 g of a nonylphenol-ethylene oxide addition product (ARKOPAL N 080, a commercially available product of Hoechst Aktiengesellschaft, Frankfurt/Main) and the suspension was mixed within 30 minutes with 232 g of $P_2O_5$. The material in the flask was heated to 80° C. until the magnesium oxide was found to have been completely dissolved. After termination of the reaction, the reaction product was cooled down to room temperature. It assumed a pasty consistency. The product contained 0.9 weight % of water and was completely soluble in benzene and tetrachloroethylene.

EXAMPLE 7

The procedure was as in Example 6, but 2000 g of the nonylphenol-ethylene oxide addition product was reacted with 232 g of $P_2O_5$ and 250 g of barium oxide. The cold product was very viscous and contained 0.6 weight % of water. It was soluble in organic solvents, e.g. in toluene, dioxane, butyl acetate and tetrachloroethylene. Minor impurities of barium oxide and barium phosphate were removed by filtering the organic solution of the reaction product.

EXAMPLE 8

1129 g of phenol and 448 g of nickel oxide were mixed in a kneader and the resulting mixture was admixed within 10 minutes with 852 g of phosphorus pentoxide. The mixture heated spontaneously to about 40° C. and became liquid. After a reaction period of 2 hours at 40° C. and a further 6 hours at 80° C., a dark green mass which was plastic and viscous at 20° C., was obtained. The mass was treated with diethylether and the phosphoric acid ester salt was obtained in the form of a pale green fine powder. It contained 0.4 weight % of water.

EXAMPLE 9

A mixture of 1500 g of isotridecyl alcohol and 611 g of ZnO placed in a kneader and preheated to 32° C. was admixed within 40 minutes with 532 g of $P_2O_5$, whereby the temperature increased gradually to 50° C. Next, the reaction mixture was heated for 4 hours to 80° C. The product so obtained was cooled down to 0° C. and a slightly plastics mass was obtained which was soluble in petroleum ethers with a boiling range of 60° to 80° C., with the exception of a minor residue which consisted essentially of unreacted ZnO. The reaction product was extracted with ether, the solvent was evaporated and the acid zinc salt of isotridecyl phosphate was obtained in the form of a rubber-like substance, which contained 21.9 weight % of $P_2O_5$ and 13.3 weight % of Zn.

EXAMPLE 10

1710 g of a commercial mixture of partially branched aliphatic alcohols with 16 to 19 carbon atoms, 340 g of $Na_2CO_3$ and 455 g of $P_2O_5$ were intensively mixed at room temperature in a kneader and heated with caution. At 40° C., $CO_2$ began to be evolved and ceased to be evolved after about 2 hours, after heating to a final temperature of 80° C. The salt obtained on cooling was a viscous paste.

I claim:
1. In a process for making a product, which consists essentially of an acid orthophosphoric acid ester salt and contains at most about 1 weight % of water, and of which the inert ester group R (inert with respect to the reactants) being an alkyl, cycloalkyl, polyalkoxyalkyl, aryl, polyalkoxyaryl, alkaryl or aralkyl group contains 1 to 50 carbon atoms, whereby the carbon chain or ring of the ester group R and the salt-forming cation M is a mono- or bivalent metal ion or an ammonium ion, the improvement which comprises: reacting, at temperatures of about 0° to 150° C., with thorough agitation, molar proportions of $P_2O_5$ and of a compound of the general formulae $M_2O$, $M_2CO_3$, MO or $MCO_3$ with $2/m$ mol of an at least partially liquid or molten organic hydroxyl compound of the general formula $R(OH)_m$, in which formulae the substituents M and R have the meanings given above and $m$ is a number of 1 to 4; terminating the reaction, cooling the resulting reaction product and pulverizing it, if desired.

2. The process as claimed in claim 1, wherein the salt-forming cation M is an alkali metal ion, alkaline earth metal ion, an alkyl or aryl-substituted ammonium ion or a bivalent cation of an element having an atomic number of 25 to 30.

3. The process as claimed in claim 1, wherein $P_2O_5$ is reacted with an organic hydroxyl compound selected from stearyl alcohol, dodecyl alcohol, cyclohexanol, phenol, polyethylene glycol, isotridecyl alcohol, nonylphenolpolyglycol ether, an addition product of stearyl alcohol and 8 mols of ethylene oxide, a commercial mixture of partially branched aliphatic alcohols having 16 to 19 carbon atoms, or trishydroxymethylphosphine oxide.

4. The process as claimed in claim 1, wherein the reactants are reacted at temperatures of 20° to 100° C., depending on the consistency of the organic hydroxyl compound.

5. The process as claimed in claim 1, wherein the reaction product contains at least about 85 weight % of acid orthophosphoric acid ester salt.

* * * * *